United States Patent [19]

Kasahara et al.

[11] Patent Number: 5,793,199
[45] Date of Patent: Aug. 11, 1998

[54] METHOD AND APPARATUS FOR DETERMINING MAGNETIC POWDER CONCENTRATION BY USING THE ELECTROMAGNETIC INDUCTION METHOD

[75] Inventors: Riichiro Kasahara; Yoshihisa Nozawa; Masanori Miyoshi, all of Osaka; Osamu Kitamura, Nishinomiya, all of Japan

[73] Assignee: New Cosmos Electric Co., Ltd., Osaka, Japan

[21] Appl. No.: 748,471

[22] Filed: Nov. 8, 1996

[30] Foreign Application Priority Data

Nov. 10, 1995 [JP] Japan ................................ 7-292489
Sep. 4, 1996 [JP] Japan ................................ 8-233769
Oct. 28, 1996 [JP] Japan ................................ 8-285024

[51] Int. Cl.⁶ .................... G01N 27/72; G01N 27/74; G01R 33/12; G08B 21/00
[52] U.S. Cl. .............................. 324/204; 324/239
[58] Field of Search ................. 324/204, 239, 324/240, 241; 118/689, 712; 399/30, 63; 73/53.07, 61.42; 340/631

[56] References Cited

U.S. PATENT DOCUMENTS

| | | |
|---|---|---|
| 3,433,057 | 3/1969 | Halsey . |
| 4,255,711 | 3/1981 | Thompson . |
| 4,613,815 | 9/1986 | Christel, Jr. . |
| 4,651,092 | 3/1987 | Brunsch et al. ............... 324/204 |
| 4,859,942 | 8/1989 | Charton et al. . |
| 4,878,019 | 10/1989 | Tsaprazis et al. . |
| 5,001,424 | 3/1991 | Kellett et al. . |
| 5,041,856 | 8/1991 | Versonesi et al. . |
| 5,278,500 | 1/1994 | Seitz . |
| 5,315,243 | 5/1994 | Kempster et al. . |
| 5,357,197 | 10/1994 | Sorkin . |
| 5,404,100 | 4/1995 | Burnett et al. . |
| 5,444,367 | 8/1995 | Kempster et al. . |
| 5,502,378 | 3/1996 | Atteberry et al. . |
| 5,528,138 | 6/1996 | Rumberger et al. . |
| 5,537,037 | 7/1996 | Otaka et al. . |

FOREIGN PATENT DOCUMENTS

0470368  2/1992  European Pat. Off. .
WOA8902083  3/1989  WIPO .

*Primary Examiner*—Walter E. Snow
*Attorney, Agent, or Firm*—Felfe & Lynch

[57] ABSTRACT

A method of determining a concentration of magnetic powdery material in a sample is disclosed. In this method, a pair of series-connected exciting coils are disposed in such a manner that magnetic fields generated from the respective exciting coils oppose to each other. A detecting coil is disposed at a position where the magnetic fields from the pair of exciting coils cancel out each other. A sample mixed with magnetic powder is inserted into one of the pair of exciting coils. Then, the method detects a voltage induced in the detecting coil in association with the insertion of the sample into the exciting coil and determines the concentration of the magnetic powder in the sample based on the detected voltage.

20 Claims, 13 Drawing Sheets

METHOD AND APPARATUS FOR DETERMINING MAGNETIC POWDER CONCENTRATION BY USING THE ELECTROMAGNETIC INDUCTION METHOD

BACKGROUND OF THE INVENTION

1. Field of the Invention

The present invention relates to a method of determining a concentration of magnetic powderly material, e.g. iron powder, mixed into lubricant such as lubricant oil, grease or the like, so as to diagnose indirectly mechanical deterioration exemplified by frictional wear of bearings used in various machines. The invention also relates to an apparatus used in the method.

2. Description of the Related Art

As an apparatus for determining a concentration of magnetic powderly material in a sample, there is known one utilizing the atomic absorption spectrometry. This method is based on the principle that when lubricant containing metal particles is brought near a high-temperature flame (e.g. airacetylene flame), the metal particles in the lubricant are released into the state of free atoms to absorb ray of a predetermined wavelength (e.g. the ray of 2.2483 angstrom wavelength in the case of iron). Another type of known apparatus for this application utilizes the differential-detecting coil magnetic induction. This apparatus, as shown in FIG. 12, includes an exciting coil L4 disposed along an axis, and a detecting coil L5 and a compensating coil L6 disposed on opposed sides across the exciting coil L4 on the same axis. The apparatus further includes a differential amplifier 3 for amplifying a differential between voltages induced in the detecting coil L5 and the compensating coil L6 respectively when a sample S mixed with magnetic powder, i.e. a container in which subject lubricant is stored in a sealed state, is inserted from the side of the detecting coil L5 into the exciting coil L4, whereby the amplified voltage differential may be detected.

However, in the case of the former type apparatus using the atomic absorption spectrometry, the apparatus requires such components as a special light source such as a hollow cathode lamp, acetylene gas burner for generating the high-temperature flame, a wavelength spectrometer using prisms or the like and also a photoelectric converter. Accordingly, the entire apparatus tends to be large and costly.

On the other hand, in the case of the latter type apparatus using the differential-detecting coiL magnetic induction, there is the problem of measurement error due to the so-called span variation. Namely, the impedance of the exciting coil varies according to the ambience temperature, so that for subject lubricant of a same concentration its measured value differs according to the temperature variation. For this reason, especially when the subject lubricant is sampled from a rotary machine, the sampled lubricant has a temperature higher than the ambient temperature. Hence, the measured value will remain unstable for a long period until the lubricant temperature drops to the ambient temperature.

In view of the above-described drawbacks of the convention, a primary object of the present invention is to provide a method and an apparatus which can solve the drawbacks and can provide more accurate measurement at lower apparatus costs.

SUMMARY OF THE INVENTION

For accomplishing the above-noted object, a method of determining a concentration of magnetic powderly material in a sample, according to the present invention, comprises the steps of:

arranging a pair of series-connected exciting coils in such a manner that magnetic fields generated from the respective exciting coils oppose to each other;

disposing a detecting coil at a position where the magnetic fields from the pair of exciting coils cancel out each other;

inserting a sample mixed with magnetic powder into one of the pair of exciting coils;

detecting a voltage induced in the detecting coil in association with the insertion of the sample into the exciting coil; and determining the concentration of the magnetic powder in the sample based on the detected voltage.

Preferably, the method further comprises the steps of:

disposing a core within the detecting coil with the core being position-adjustable along the axis of the detecting coil; and calibrating the zero point of the voltage induced in the detecting coil by adjusting the axial position of the core therein, and then effecting said step of inserting the sample into one of the exciting coils.

An apparatus for determining a concentration of magnetic powder in a sample, according to the present invention, comprises:

a pair of series-connected exciting coils arranged in such a manner that magnetic fields generated respectively therefrom oppose to each other, one of the exciting coils being capable of receiving therein the sample mixed with magnetic powder;

a detecting coil disposed at a position where the magnetic fields generated from the pair of exciting coils cancel out each other; and measuring means for measuring a voltage induced in the detecting coil in association with insertion of the sample into the one exciting coil, the magnetic power concentration being derived from the measured induced voltage.

Preferably, the apparatus further comprises a core which is disposed within the detecting coil to be position-adjustable along the axis of the detecting coil.

According to the above-described method construction and apparatus construction, when the sample is not inserted into the one exciting coil, or when the inserted sample does not contain any magnetic powderly material, the magnetic fields from the pair of exciting coils cancel out each other, so that no voltage is induced in the detecting coil. On the other hand, if a sample containing some magnetic powderly material is inserted into the exciting coil, this causes change in the magnetic permeability within this exciting coil alone into which the sample has been inserted. As a result, the balance between the magnetic fields of the two exciting coils is lost, whereby an induced voltage is developed in the detecting coil.

As the magnetic permeability in the exciting coil varies in proportion to the concentration of the magnetic powder contained in the sample, the magnetic powder concentration may be readily derived from the measured induced voltage of the detecting coil.

Further, as described hereinbefore, the one exciting coil may be subjected to a local temperature variation due to the insertion of the hot sample into it, resulting in variation in the impedance of this coil, which variation results in turn in variation in the induced current. However, according to the above-described construction of the present invention, there are provided a pair of series-connected exciting coils, Therefore, the induced current variation in the one exciting coil results in that in the other exciting coil series-connected thereto, so that no change occurs in the magnetic balance therebetween, hence, no change in the zero point.

Moreover, if such local temperature variation occurs in one exciting coil, the other exciting coil which is disposed apart from the one coil is less affected by the temperature variation. Thus, resulting variation in the combined impedance of these two coils will be less than impedance variation, due to local temperature variation, in the single exciting coil as employed by the conventional differential-detecting coil magnetic induction construction. Consequently, the invention's construction can advantageously reduce the measurement error due to the span variation.

As a result of the above, with the method or apparatus according to the present invention, it has become possible to accurately determine the magnetic powder concentration in a sample even when this sample comprises lubricant sampled from a rotary machine and thus having a higher temperature than the ambience. And, this accurate determination may be made speedily without having to wait until the temperature of the sample becomes stable.

Consequently, the invention has fully achieved its intended object of providing a method and a compact apparatus which can solve the drawbacks of the prior art by enabling more accurate measurement at lower apparatus costs.

According to the further feature of the invention there is provided also a core, e.g. a ferrite core, within the detecting coil with the core being position-adjustable along the axis of the detecting coil. Even when no sample is inserted into the exciting coil or when the inserted coil does not contain any magnetic powder, an induced voltage may be erroneously developed in the detecting coil due to e.g. inadvertent shifting of the detecting coil from its proper position. In such case, according to the above construction, the zero-point calibration may be conveniently effected by adjusting the position of the core, without changing the position of the detecting coil. This construction provides the further advantage of reducing the magnetic resistance within the detecting coil, hence improving its detection sensitivity.

According to a further aspect of the invention, the method of determining magnetic powder concentration in a sample comprises the further steps of:

detecting insertion or non-insertion of the sample into the exciting coil;

obtaining zero-point calibrating data when no sample insertion is detected; and effecting an automatic zero-point calibration when sample insertion is detected, based on the zero-point calibrating data obtained immediately prior to the detection of sample insertion.

Further, the magnetic powder concentration in the sample may be determined based on a voltage induced in the detecting coil upon completion of the insertion of the sample into the exciting coil or upon lapse of a predetermined time period after the insertion of the sample into the exciting coil.

Further, according to a further aspect of the invention, the magnetic powder concentration determining apparatus further comprises:

processor means for outputting the magnetic powder concentration in the sample based on the voltage induced in the detecting coil;

sample detecting means for detecting insertion or non-insertion of the sample into the exciting coil; and calibrating means capable of inputting zero-point calibrating data when the sample detecting means detects non-insertion of the sample and then effecting automatic zero-point calibration when the sample detecting means detects insertion of the sample, based on the zero-point calibrating data inputted immediately prior to this detection of sample insertion by the sample detecting means.

That is, the calibrating means periodically inputs the zero-point calibrating data, i.e. data used for resetting the output of the detecting coil to zero, when the sample detecting means detects no insertion of sample into the exciting coil. Then, when the sample detecting means detects insertion of sample, the calibrating means automatically effects zero-point calibration based on the immediately previously inputted zero-point calibrating data, regardless of the operator's awareness of its necessity. Accordingly, the zero-point calibration may be effected appropriately at the time of measurement.

Preferably, the processor means outputs the magnetic powder concentration based on a voltage induced in the detecting coil upon completion of the insertion of the sample into the exciting coil or upon lapse of a predetermined time period after the insertion of the sample into the exciting coil.

The measurement by the processor means should be effected after the sample has been completely and reliably inserted into the coil. Yet, when the sample insertion or non-insertion cannot be determined reliably, or when the sample of the hot lubricant sampled from a rotary machine is inserted into the coil, the ambience temperature about the coil may vary, thus changing the zero-point. In such case, the output from the apparatus will change according to time, so that the operator will find it difficult to read the output value. Then, according to the above feature, the magnetic powder concentration is determined based on a voltage induced in the detecting coil upon completion of the insertion of the sample into the exciting coil or upon lapse of a predetermined time period after the insertion of the sample into the exciting coil. With this, the magnetic powder concentration may be determined accurately.

In the above, the timing upon completion of the insertion of sample into the coil or upon lapse of a predetermined time period after sample insertion means the timing when the detecting means detects the insertion of the sample or when stability of the magnetic powder concentration value has been confirmed, or when a predetermined time period has lapsed after the detection of the sample insertion.

According to a still further aspect of the present invention, the one exciting coil is series-connected with a thermosensitive element having NTC (negative temperature coefficient) characteristics so as to maintain constant the current in the exciting coil against variation in the ambience temperature.

In general, a resistance component R of a coil may be expressed by a following equation.

$$R = R_o (1 + 2\Delta t)$$

where, $R_o$ is the resistance of the coil, 2 is the temperature coefficient of the coil, $\Delta T$ is a temperature variation.

Then, if the coil is series-connected with a thermosensitive element, e.g. a thermistor, having the NTC characteristics (i.e. the characteristics of negative temperature coefficient that the resistance value decreases in response to increase in the temperature), in association with increase in the temperature, the resistance of the coil increases, but that of the thermosensitive element decreases, so that the combined resistance may be maintained constant, thereby to maintain constant the current in the exciting coil.

Further, a power source for supplying exciting power to the exciting coils may be comprised of a constant-current source.

With this construction too, the coil current may be maintained constant, regardless of temperature-associated variation in the resistance of the exciting coil.

Preferably, the exciting coil is formed of a wire whose resistance has a temperature coefficient of $5 \times 10^{-5}$ or less.

With the above, the coil is constructed from a wire with resistance of very small temperature coefficient, e.g. a manganin (Mn-Ni-Cu alloy) wire. This feature too may minimize the influence from the temperature under ordinary application conditions.

According to a still further aspect of the invention, the power source for the exciting coil outputs a square wave current, and the detecting coil constitutes a part of an oscillator circuit.

With the above construction, the power source for supplying the exciting current to the exciting coil may be constructed from an inexpensive square-wave supplying power source and e.g. a capacitor element is parallel-connected to the detecting coil thereby to constitute together an oscillator circuit, and the apparatus samples the output of this resonance circuit for the concentration determination. Then, the output in the form of a sine-wave output may be obtained while avoiding noise generation due to parasitic oscillation which would result in the output from the detecting coil alone.

Consequently, the apparatus having the above construction can minimize noise generation and provide accurate measurement, while using an inexpensive power source.

Further and other objects, features and effects of the invention will become more apparent from the following more detailed description of the embodiments of the invention with reference to the accompanying drawings.

DETAILED DESCRIPTION OF THE PREFERRED EMBODIMENTS

Preferred embodiments of a magnetic powder concentration determining method and apparatus both relating to the present invention will be described in details with reference to the accompanying drawings.

Figure 1:
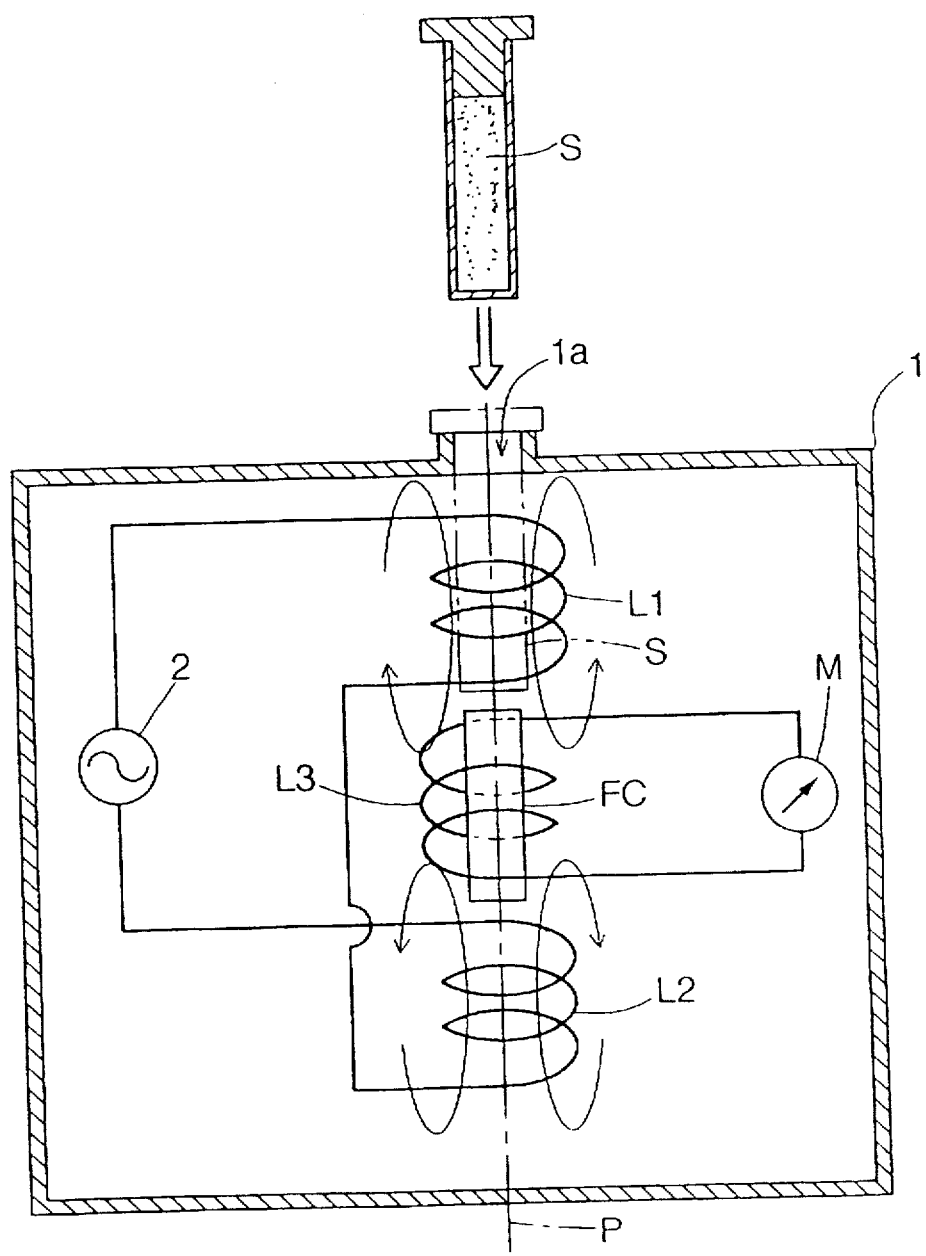
FIG. 1 is a schematic construction view of a magnetic powder concentration determining apparatus according to one preferred embodiment of the present invention.

FIG. 1 shows an apparatus according to one embodiment of the invention. This apparatus includes a pair of series-connected identical exciting coils L1, L2 housed within a casing 1 and disposed along a common vertical axis P so that magnetic fields from the respective coils L1, L2 oppose to each other. The apparatus further includes a detecting coil L3 disposed centrally between the exciting coils L1, L2 on the same common axis P at a position where the magnetic fields of the exciting coils L1, L2 cancel out each other. The exciting coils L1, L2 are connected with a power source 2 which supplies the coils L1, L2 with an exciting current at 30 kHz to 50 kHz approximately.

The casing 1 defines, in an upper face thereof and immediately above the upper exciting coil L1, an insertion hole 1a, through which a non-metallic (e.g. glass, resin or the like) sample container storing therein in a sealed state a sample S mixed with magnetic powderly material. Then, the sample container inserted through the insertion hole 1a has its un-inserted upper edge rested on the upper face of the casing 1 and has its inserted portion maintained within the exciting coil L1.

The apparatus further includes an AC voltmeter as measuring means M connected with the detecting coil L3 for detecting a voltage induced in the detecting coil L3 in association with the insertion of the sample container. More particularly, with the container insertion, in proportion to a concentration of the magnetic powder contained in the sample S, the magnetic permeability inside the exciting coil L1 varies, resulting in change in the magnetic balance. This change in the magnetic balance is obtained through the measurement of the induced voltage on the detecting coil L3 and from this, the concentration of the magnetic powder contained in the sample S is derived.

A ferrite core as an iron core FC having spiral ridges in its periphery is threaded into the detecting coil L3, with the core being position-adjustable along the axis of the coil L3. Namely, even when the sample S is not inserted into the exciting coil L1 or when the inserted sample S does not contain any magnetic powder, an induced voltage may be erroneously generated due to inadvertent shifting in the position of the detecting coil from its proper position. Then, to remedy this, with the above-described construction, a zero-point calibration may be readily effected by adjusting the position of the core FC along the axis of the detecting coil L3, without having to change the position of the coil L3. This construction provides the further advantage of reducing the magnetic resistance inside the detecting coil L3 thereby to improve its detection sensitivity.

Figure 2:
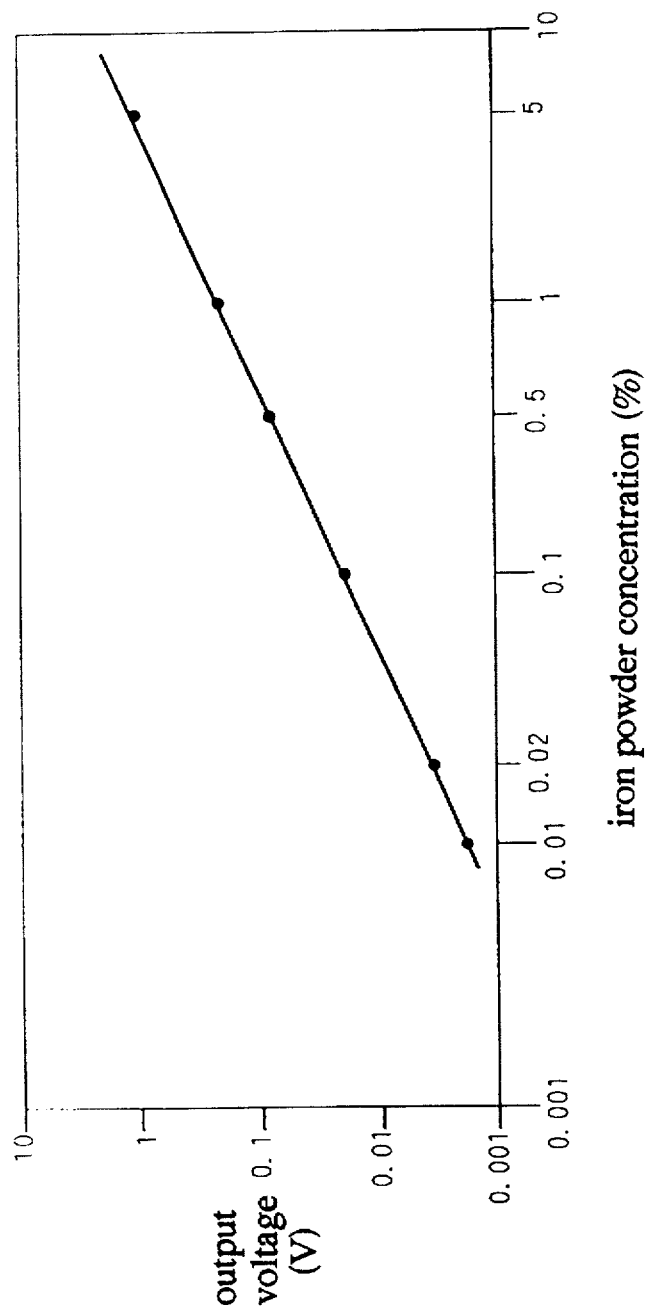
FIG. 2 is a graph showing characteristics of output voltage-magnetic powder concentration.

The magnetic powder concentration determining apparatus having the above-described construction was experimentally used for 10 times of measurement under the ambience conditions of 25.8° C., 61% Rh, using a 2.5 ml glass container storing therein grease containing 0.01% to 5% of iron powder. And, an average value was calculated from the total ten measured values. The results are shown in FIG. 2. As shown, it was found that there exists a substantially linear relationship between the magnetic powder concentration and the output voltage.

In the above, a span adjustment was made so that the voltage of 1V will be outputted in response to the sample having 5% magnetic powder concentration.

Regarding a span variation which occurred in measurement when a hot sample was introduced into the above-described apparatus according to the invention, a control experiment was conducted, with using a conventional apparatus operating under the conventional differential-detecting coil magnetic induction. The results of this control experiment will be described next.

Figure 3:
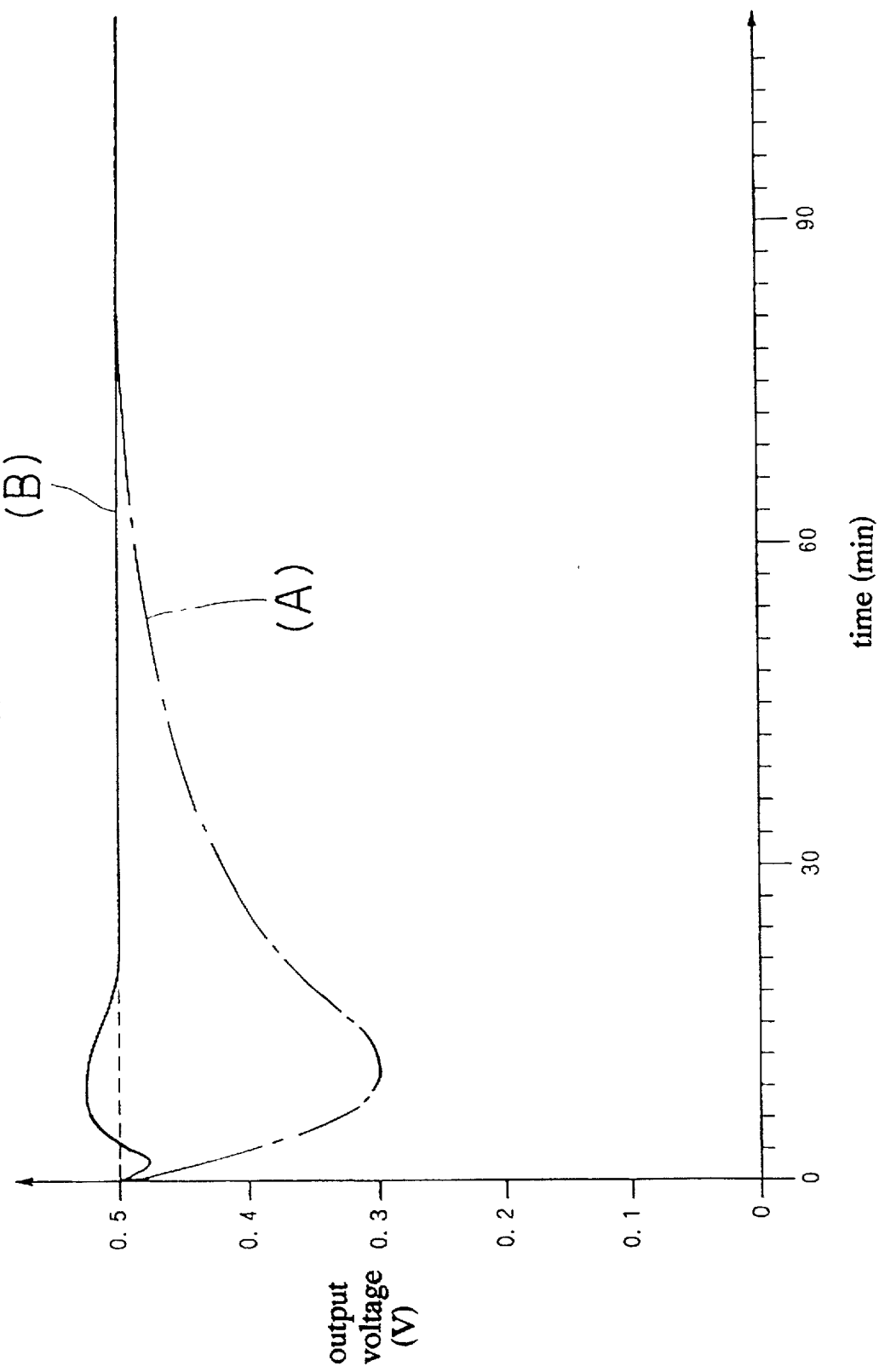
FIG. 3 is a graph showing temperature-dependent characteristics of magnetic powder concentration output.

In this experiment, the invention's apparatus and the conventional apparatus were installed at the room temperature of about 25° C. and used for measuring 0.5% concentration sample which was temperature-adjusted to about 60° C. by means of a thermostat. The results are shown in FIG. 3. As may be apparent from this graph, it was found that the output (A) from the conventional apparatus using the differential-detecting coil magnetic induction varied significantly in accordance with lapse of time while the output (B) from the invention's apparatus varied little regardless of time lapse.

Figure 4:
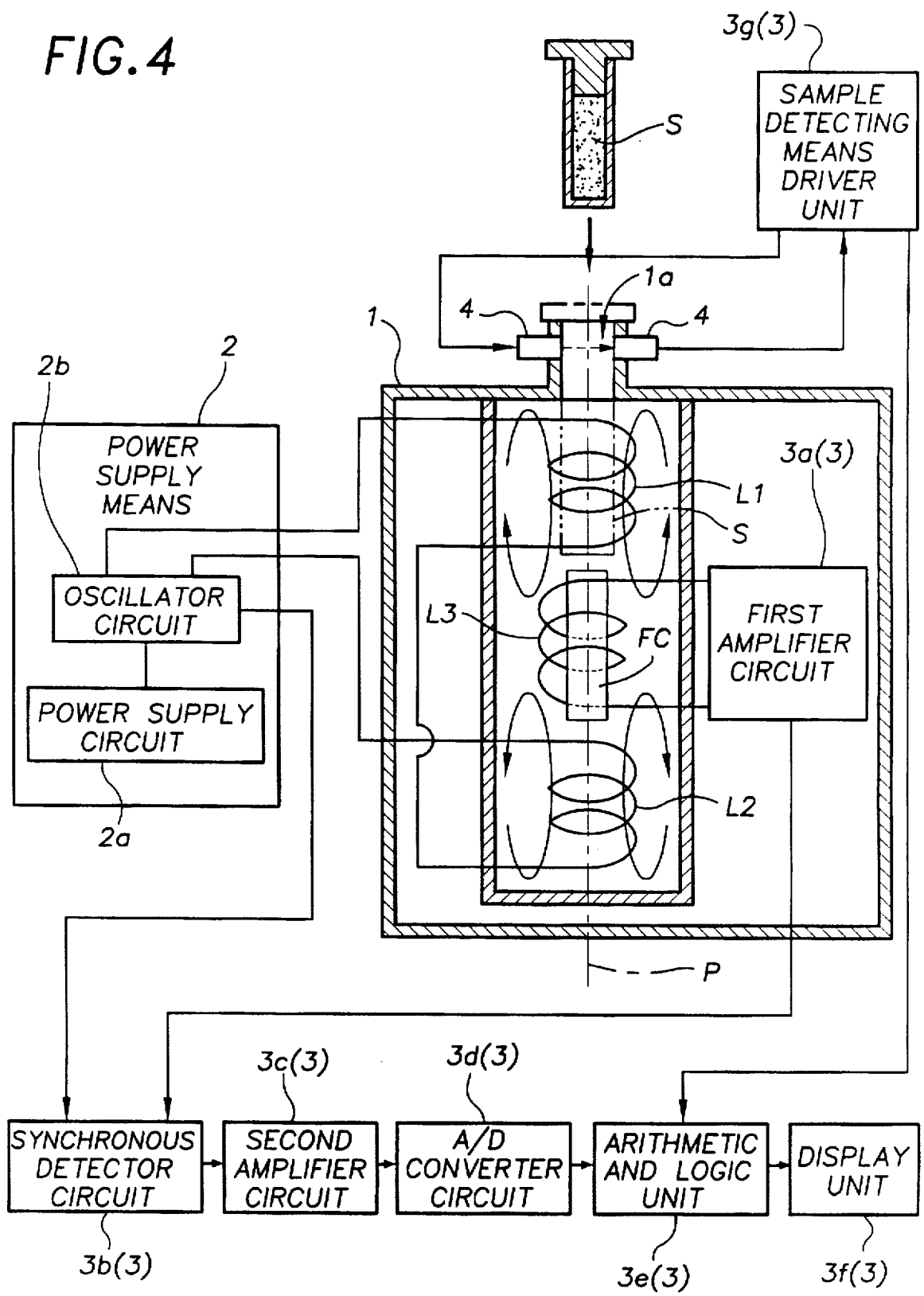
FIG. 4 is a schematic construction view of a magnetic powder concentrating determining apparatus relating to a further embodiment of the present invention.

Next, other embodiments of the invention will be described. [1] A magnetic concentration determining apparatus according to a further embodiment is shown in FIG. 4. Just like the apparatus of the foregoing embodiment shown in FIG. 1, this apparatus includes a pair of series-connected identical exciting coils L1, L2 housed within a casing 1 and disposed along a common vertical axis P so that magnetic fields from the respective coils L1, L2 oppose to each other. The apparatus further includes a detecting coil L3 disposed centrally between the exciting coils L1, L2 on the same common axis P at a position where the magnetic fields of the exciting coils L1, L2 cancel out each other. The pair of exciting coils L1, L2 and the detecting coil L3 are all housed within a magnetic sealing member, thereby to constitute together a measuring means. The exciting coils L1, L2 are connected with a power source 2 which supplies the coils L1, L2 with an exciting current. Further, in this embodiment, the apparatus further includes a processor means 3 for calculating the magnetic powder concentration from the output signal from the detecting coil L3.

The casing 1 defines, in an upper face thereof and immediately above the upper exciting coil L1, an insertion hole 1a, through which a non-metallic (e.g. glass, resin or the like) sample container storing therein in a sealed state a sample S mixed with magnetic powderly material. Then, the sample container inserted through the insertion hole 1a has its un-inserted upper flange rested on the upper face of a support portion 1b of the casing 1 and has its inserted portion maintained within the exciting coil L1. At the support portion 1b, there is provided a sample detecting means 4 comprised of a photoelectric sensor for detecting insertion or non-insertion of the sample container into the exciting coil L1. Incidentally, this sample detecting means 4 may be comprised also of a mechanical sensor such as a micro switch, in place of the photoelectric sensor.

The power source 2 includes a power supply circuit 2a and a generator circuit 2b for outputting an AC exciting current of about 30 kHz to 200 kHz. The processor means 3 includes a first amplifier circuit 3a for amplifying the output signal from the detecting coil L3, a synchronous detector circuit 3b for detecting the amplified signal in synchronism with the output signal from the generator circuit 2b and then outputting a DC current, a second amplifier circuit 3c for amplifying the output of the synchronous detector circuit 3b, an A/D converter circuit 3d for quantizing the amplified signal from the second amplifier circuit 3c, an arithmetic and logic unit 3e for obtaining, from the digital data, the concentration of the magnetic powder contained in the sample S, according to a predetermined conversion expression, a sample detecting means driver unit 3g for driving the sample detecting means 4 to input its sample container detection signal to the arithmetic and logic unit 3e, and a display unit 3f using a liquid crystal display for displaying the result of calculation executed by the arithmetic and logic unit 3e. In operation, with the container insertion, in proportion to a concentration of the magnetic powder contained in the sample S, the magnetic permeability inside the exciting coil L1 varies, resulting in change in the magnetic balance. This change in the magnetic balance is obtained through the measurement of the induced voltage on the detecting coil L3 and from this, the concentration of the magnetic powder contained in the sample S is calculated.

A ferrite core as an iron core FC having spiral ridges in its periphery is threaded into the detecting coil L3, with the core being position-adjustable along the axis of the coil L3. Namely, even when the sample S is not inserted into the exciting coil L1 or when the inserted sample S does not contain any magnetic powder, an induced voltage may be erroneously generated due to inadvertent shifting in the position of the detecting coil. Then, to remedy this, with the above-described construction, a zero-point calibration may be readily effected by adjusting the position of the core FC along the axis of the detecting coil L3, without having to change the position of the coil L3. This construction provides the further advantage of reducing the magnetic resistance inside the detecting coil L3 thereby to improve its detection sensitivity.

Incidentally, the casing 1 mounts a self-return type span adjusting switch (not shown), whose signal is inputted to the arithmetic and logic unit 3e.

Figure 5A:
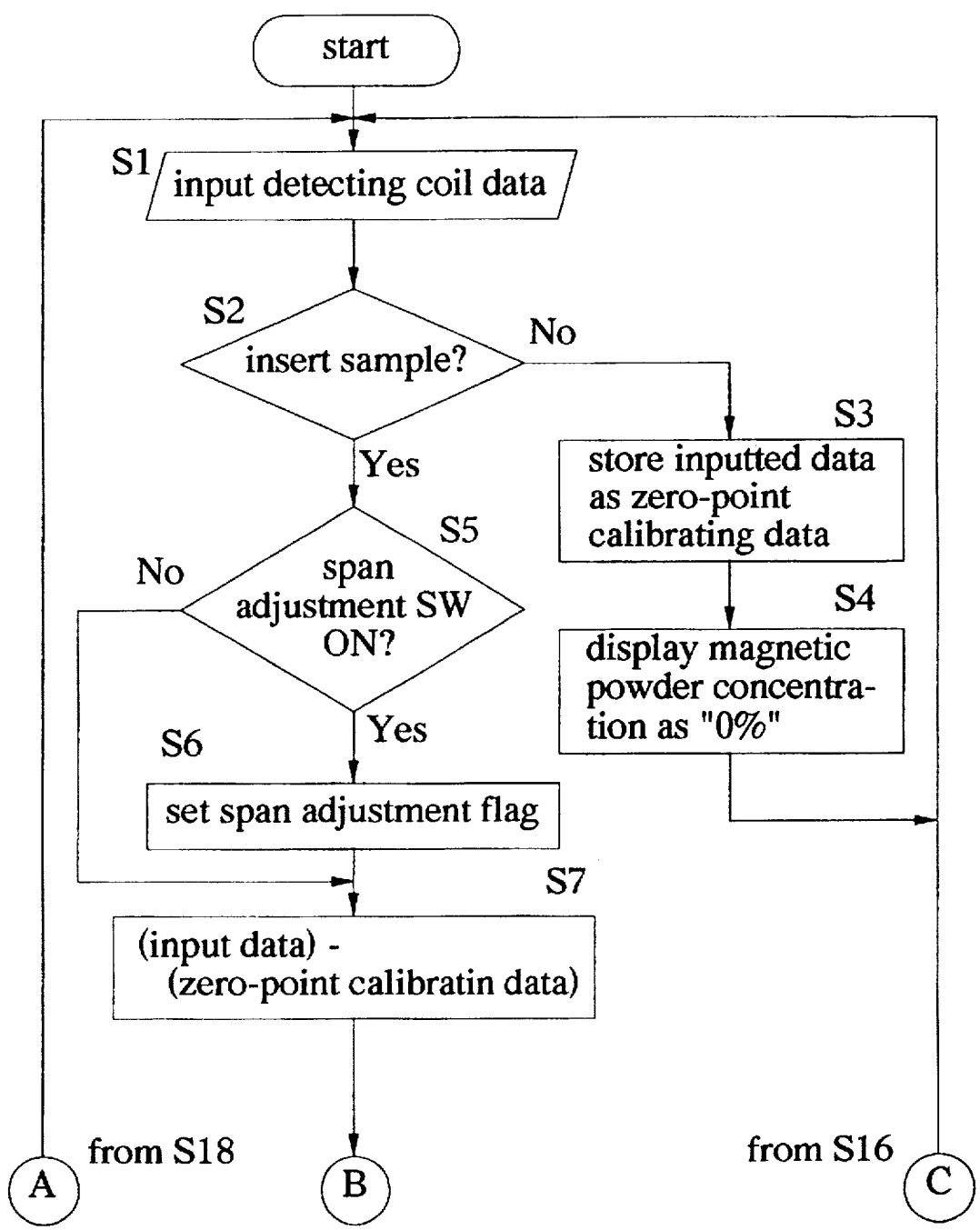
FIG. 5(a) and 5(b) are a flow chart illustrating a usage of the apparatus of FIG. 4.
Figure 5B:
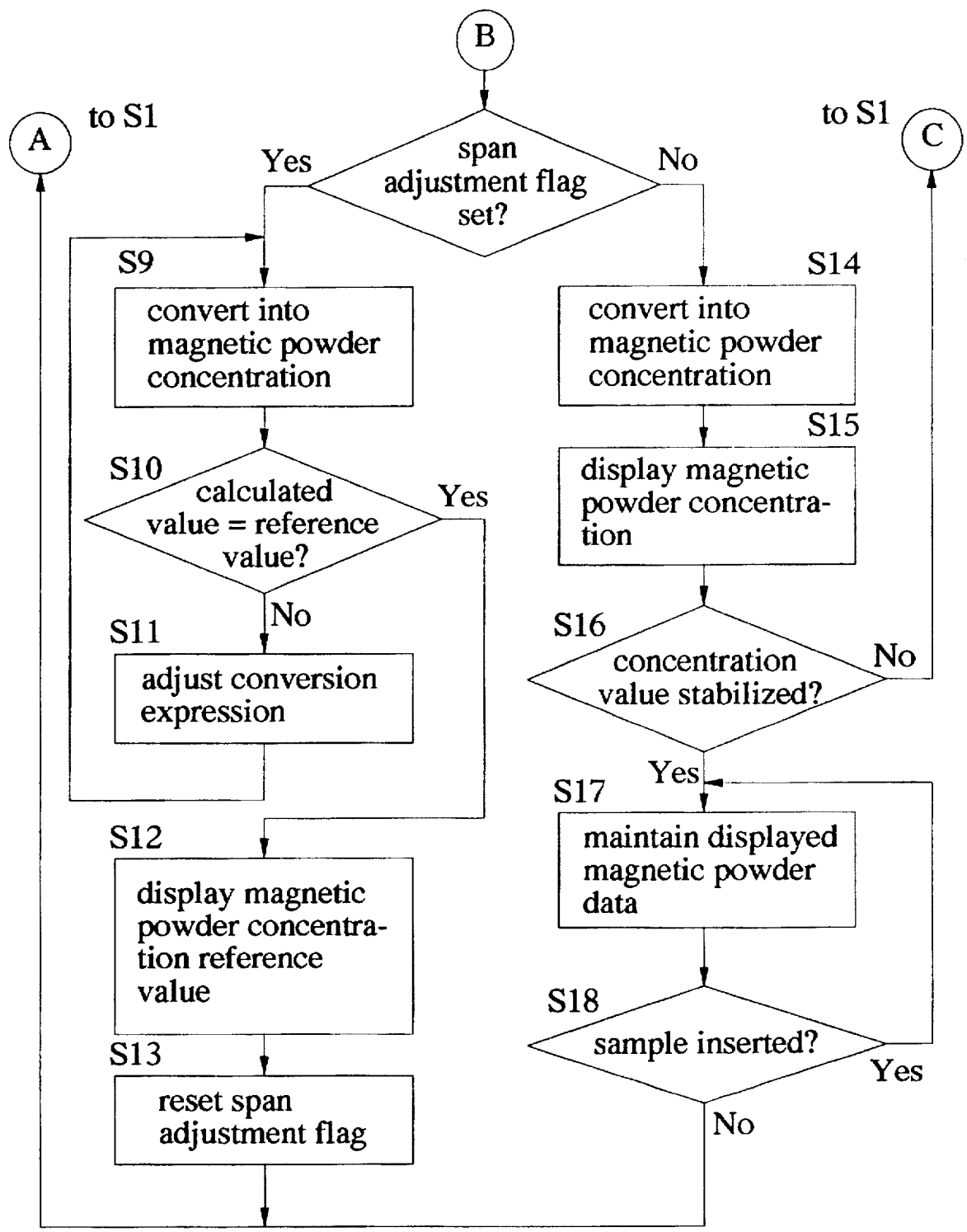

Next, the operation of the magnetic powder concentration determining apparatus having the above-described construction will be described with reference to a flow chart in FIG. 5.

With turning ON a power switch (not shown) of the apparatus, the process inputs data of the detecting coil L3 through the A/D converter circuit 3d into the arithmetic and logic unit 3e (S1). If the sample detecting means 4 detects no insertion of the sample container (S2); then, the inputted data are stored, as zero-point calibrating data, in a storage circuit (not shown) incorporated with the arithmetic and logic unit 3e and the display unit 3f displays a magnetic powder concentration being '0%' (S3, S4).

The above-described input operation of the zero-point calibrating data is effected every predetermined time period, e.g. every few hundreds of millisecond so as to be updated to the newest data. This is done for the purpose of compensating for a shift in the zero point which may have occurred after a zero-point calibration operation effected at the time of shipping of the apparatus through position adjustment of the iron core FC or change in the condition of the measuring means or the processor means 3 due to ambience temperature.

If the sample detecting means 4 detects insertion of the sample container (S2), it is then determined whether the span adjusting switch (not show) has been operated or not. If a positive-going 'ON' edge is D detected, a span adjusting flag is set up (S6).

Then, a zero-point calibration is effected by subtracting the zero-point calibrating data from the inputted data (S7), and the process proceeds to a span adjusting step if the span adjusting flag is set up. More particularly, the operator will first turn on the span adjusting switch and then insert a reference sample container having a predetermined reference concentration (sample having a magnetic powder concentration of 5%) into the exciting coil L1. In this, on the data inputted after the zero-point calibration, a predetermined conversion expression is applied to derive therefrom a magnetic powder concentration value. Then, the conversion expression is calibrated to provide a value of 5%. If this value: 5% is obtained, the display unit 3f is caused to display the magnetic powder concentration being '5%', and then the span adjusting flag is reset (S9–S13). More specifically, this adjustment is done in such a manner that voltage data derived from the input data (input voltage) with the insertion of the 5% concentration reference sample may become a predetermined value.

If it is detected at step S8 that the span adjusting flag is reset, it is determined that the span adjustment has been completed. Then, the predetermined conversion expression is applied on the data inputted after the zero-point calibration to derive therefrom a magnetic powder concentration (S14, S15). As described hereinbefore, the data input operation from the detecting coil L3 is effected every few hundreds of milliseconds (e.g. every 300 milliseconds), and this data input operation is repeatedly carried out while there remains difference between the previously inputted data and the presently inputted data. When the data having a variation amount or ratio lower than the predetermined value have been inputted for a predetermined number of times (e.g. three times) in a row, it is determined that the condition has been stabilized. Then, this concentration value is stored in the storage circuit (not shown) of the arithmetic and logic unit 3e. This stored concentration value is displayed on the display unit 3f, and this displayed data are not changed even if data inputted subsequently vary, thereby to facilitate the reading operation of the operator.

In the above, the determination as to whether the detected concentration value has been stabilized or not is made, based on whether or not the data having a variation amount or ratio lower than the predetermined value have been inputted for a predetermined number of times in a row. This operation is effected for the following reason. Namely, the concentration measurement operation should be made upon completion of insertion of the sample into the exciting coil. Yet, even when the sample detecting means 4 detects insertion of the sample container, the operator may sometimes not be able to positively determined whether the sample has been reliably inserted to the predetermined position or not. Further, when a sample of hot lubricant oil sampled from e.g. a rotary machine is inserted into the exciting coil, this insertion causes change in the ambient temperature about the coil thereby to shift its zero point. In such case, the output from the apparatus varies according to time, which makes it difficult for the operator to recognize an accurate output. The above-described operation is done for avoiding such inconveniences. Namely, after the sample detecting means 4 has detected start of insertion of the sample container and then when data having a variation amount or ration lower than the predetermined value have been inputted a few times (e.g. three times) in a row, it is determined that the setting of the sample container at the predetermined position has been completed and this value is maintained and displayed. And, the process prevents this displayed concentration value from being varied by input data variation due to subsequent temperature variation.

Accordingly, the specific measures taken to avoid the above inconveniences are not limited to those described above as long as the magnetic powder concentration is obtained based on a voltage induced in the detecting coil L3 upon completion of insertion of the sample container into the exciting coil L1 or upon lapse of a predetermined time period after insertion of the sample container into the exciting coil L1 and this obtained powder is maintained thereafter.

Figure 6:
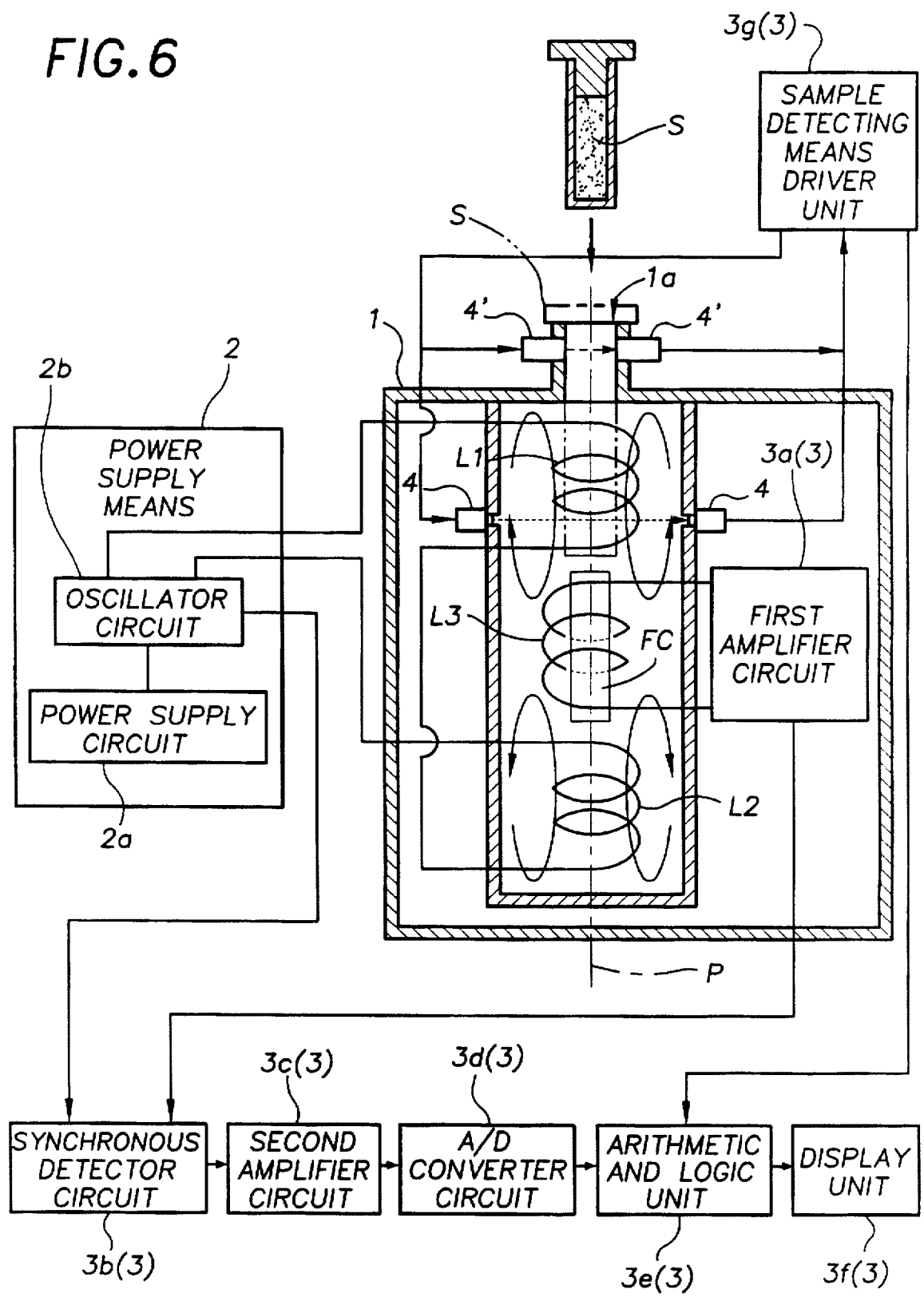
FIG. 6 is a schematic construction view of a magnetic powder concentration determining apparatus relating to a still further embodiment of the invention.

For instance, as shown in FIG. 6, it is conceivable to disposed the sample detecting means 4 comprised of a photoelectric sensor at the distal end of the exciting coil L1 adjacent the detecting coil L3 so as to detect the insertion of the sample container at the timing of completion thereof, so that data derived based on the data inputted at the time of this detection may be maintained. In this case, there is possibility that the zero-point calibrating data may be sampled in the midst of the insertion of the sample container. Therefore, it it preferred that a second sample detecting means 4' be provided at the proximal end of the exciting coil L1 adjacent the insertion hole 1a thereof, so that data inputted immediately before detection of the sample container be used as the zero-point calibrating data. Further alternatively, the target data to be maintained may be derived from data inputted upon lapse of a predetermined time period extending from the timing of detection of the sample insertion by the detecting means 4 to completion of setting of the sample to the predetermined position.

When the sample detecting means 4 detects withdrawal of the sample container, the process returns to step S1 to be ready for the next measurement (S18).

[2] In the foregoing, for effecting the automatic zero-point calibration, the output data of the detecting coil L3 inputted prior to insertion of the sample container into the exciting coil L1 are stored as zero-point calibrating data in the storing circuit (not shown) incorporated in the arithmetic and logic unit 3e, and these zero-point calibrating data are subtracted from the output data of the detecting coil L3 inputted after the insertion of the sample container into the exciting coil L1. Alternatively, for effecting the zero-point calibration, an analog construction may be employed in place of such digital computation. In this case, for example, the second amplifier circuit 3c will be comprised of an operational amplifier, and a volume circuit or a switch circuit will be provided for automatically switching over one of the input voltages to the operational amplifier, and the arithmetic and logic unit 3e will output a signal for the switch-over.

Figure 7:
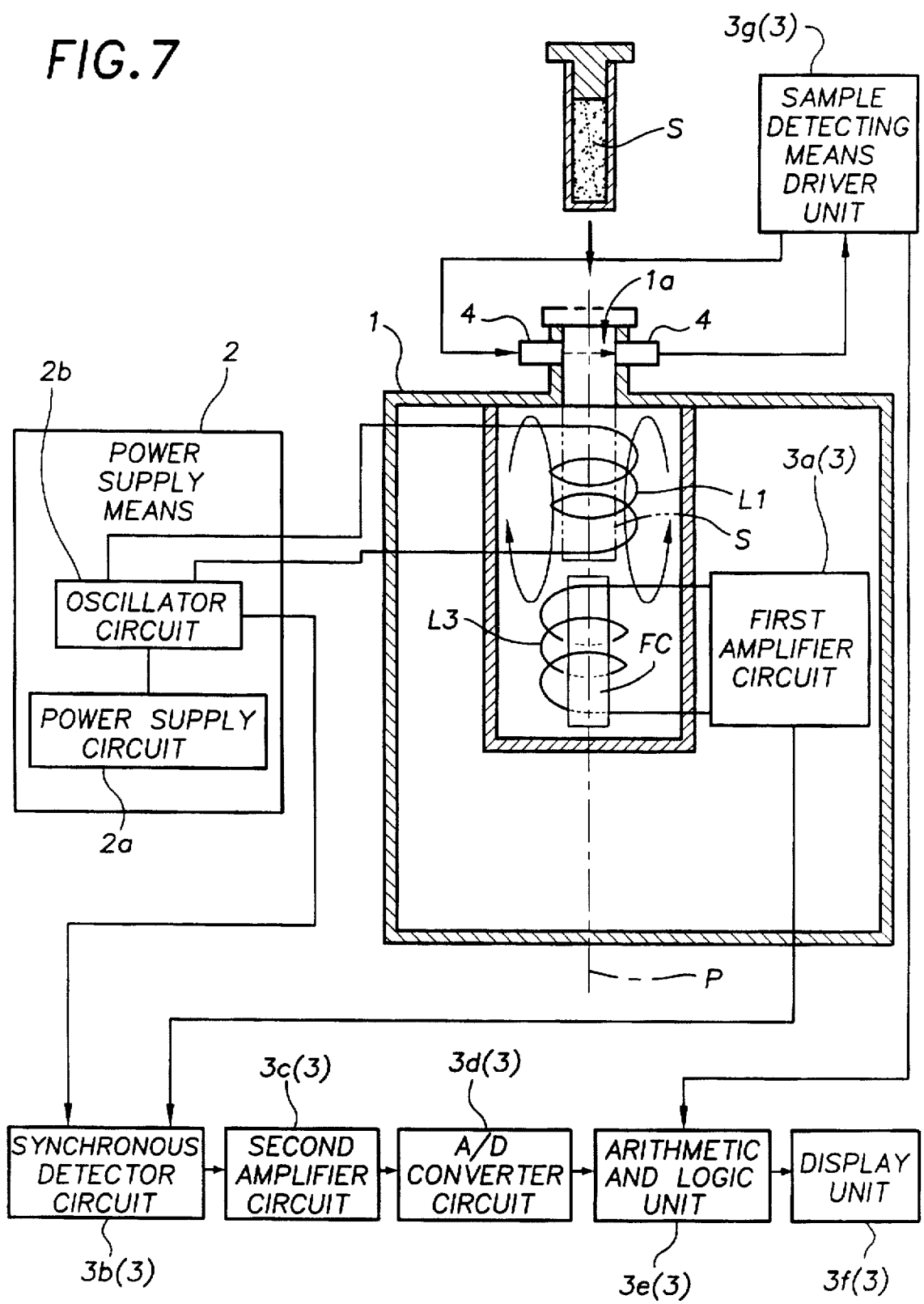
FIG. 7 is a schematic construction view of a magnetic powder concentration determining apparatus relating to a still further embodiment of the invention.

[3] The magnetic powder concentration determining apparatus may employ any specific method as long as the method is based on the electromagnetic induction. For example, instead of the magnetic-balance type electromagnetic induction described above, the apparatus may employ a more simple construction using a single exciting coil L1 and a single detecting coil L3, as shown in FIG. 7.

Figure 8:
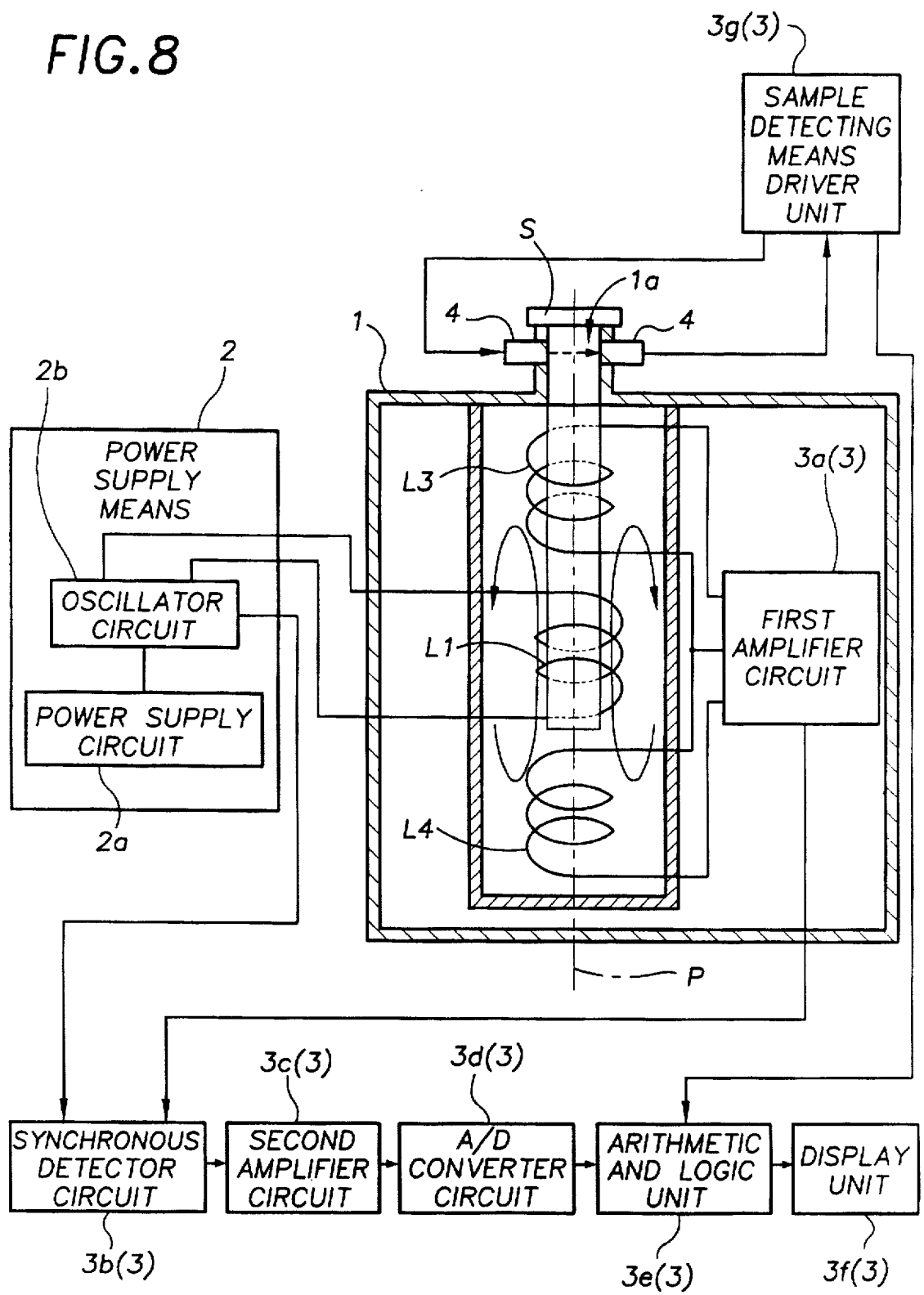
FIG. 8 is a schematic construction view of a magnetic powder concentration determining apparatus relating to a still further embodiment of the invention.

[4] Further, as shown in FIG. 8, the apparatus may employ also a differential-detecting coil electromagnetic induction construction including a single exciting coil L1 interposed between a pair of, detecting coils L3, L4. In this respect, in the case of the magnetic balance type electromagnetic induction construction, the sample container is to be inserted into either one of or both of the exciting coil and the detecting coil. Whereas, in the case of the constructions shown in FIGS. 7 and 8, the sample container is to be inserted into the detecting coil alone.

[5] In the case of the magnetic balance type electromagnetic induction construction described hereinbefore, the iron core FC is disposed within the detecting coil L3 to be position-adjustable along the axis thereof. Yet, the essential function and effect of the present invention may also be achieved without the iron core FC.

[6] In the foregoing embodiment, a pair of series-connected identical exciting coils L1, L2 are disposed on a vertical common axis so that the magnetic fields generated therefrom oppose to each other and also the detecting coil L3 is disposed on the same axis at the position where the magnetic fields of the exciting coils L1, L2 cancel out each other, namely, at the middle position between these identical exciting coils. Yet, it is not absolutely necessary for these exciting coils L1, L2 to be identical to each other. Namely, these coils L1, L2 may differ in the number of coils and/or impedance thereof. In such case, the detecting coil L3 should be disposed at any position where the magnetic fields of the coils L1, L2 cancel out each other.

[7] It is not absolutely necessary for the exciting coils L1, L2 to be disposed on one common axis, as long as their magnetic fields oppose to each other. In such case too, the detecting coil L3 will be disposed at any appropriate position where the magnetic fields of the exciting coils L1, L2 cancel out each other.

[8] A still further embodiment will be described next.

Figure 9:
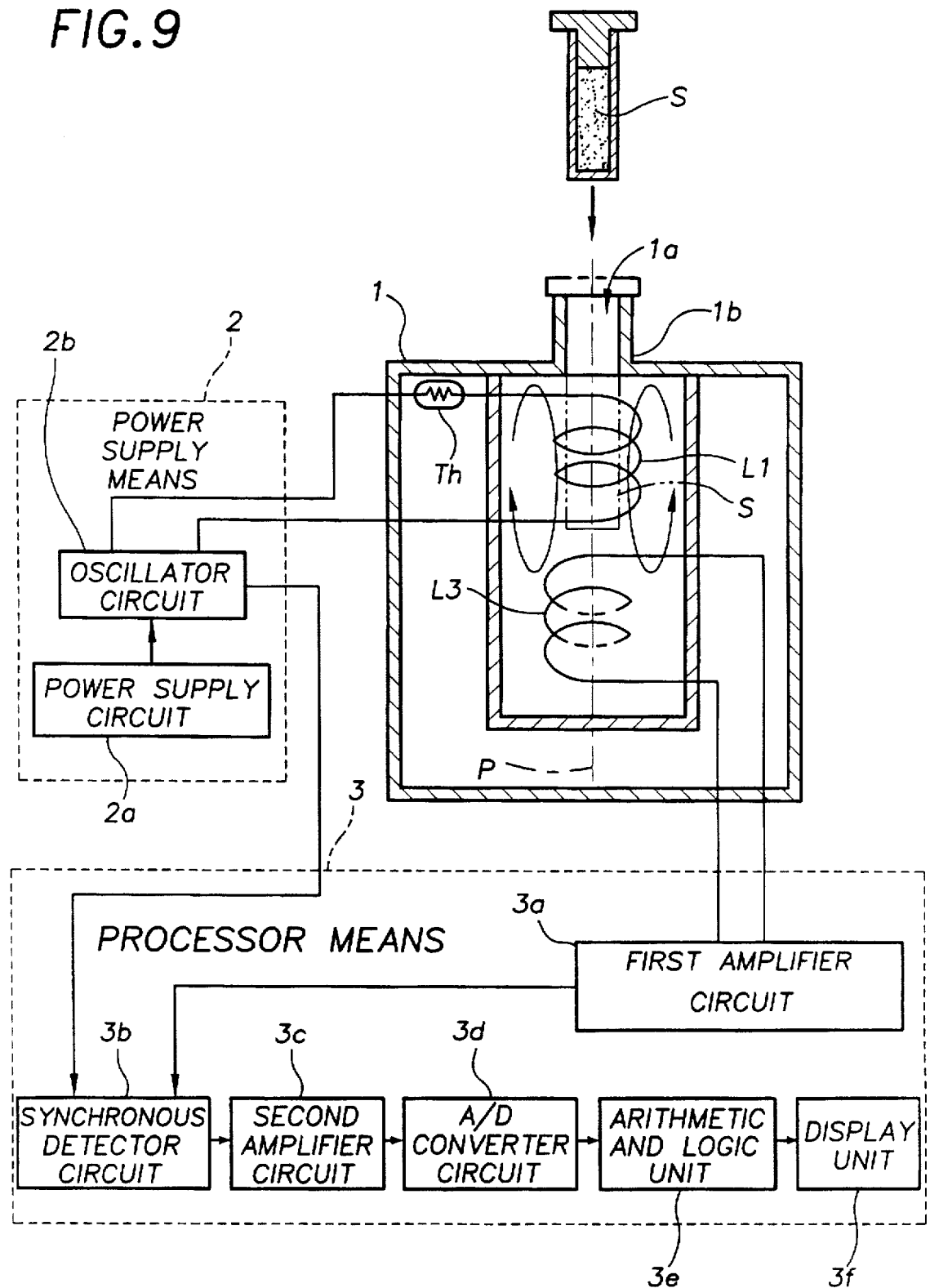
FIG. 9 is a schematic construction view of a magnetic powder concentration determining apparatus relating to a still further embodiment of the invention.

A magnetic powder concentration determining apparatus according to this embodiment, as shown in FIG. 9, comprises measuring means including an exciting coil L1 to which a thermistor Th is series-connected and a detecting coil L3 disposed on a same axis P as the exciting coil L1, i.e. on the magnetic path of the exciting coil L1, with the coils L1, L3 being housed together within a magnetic sealed member; a power source means 2 for supplying an exciting current to the exciting coil L1; and a processor means 3 for calculating a magnetic powder concentration from an output signal from the detecting coil L3. The measuring means, the power source means and the processor means are housed in a housing 1.

The thermistor series-connected to the exciting coil L1 is a thermosensitive element having NTC characteristics, i.e. a negative temperature coefficient that the resistance decreases in response to increase in the temperature. In operation, in response to the coil resistance which increases in response to rise in the coil temperature due to ambience temperature variation or insertion of hot sample container, the resistance of the thermosensitive element decreases correspondingly, thereby to maintain constant the current in the coil, whereby the zero-point shift or output span variation may be effectively avoided. The thermosensitive element is not limited to the thermistor. Instead, this may utilize the temperature characteristics of a PN junction of a semiconductor.

If such thermosensitive element having the NTC characteristics is provided, in series connection, not only to the exciting coil L1, but also to the detecting coil L3, the temperature compensating effect may be further enhanced.

[9] In the above alternative embodiment, a thermosensitive element is employed for the temperature compensation. For the same purpose, it is also conceivable to construct the power source means 2 from a constant-current power source. That is, although the coil resistance increases in response to the coil temperature, the coil current may be maintained constant by using the constant current source as the exciting current source. In this case too, if the thermosensitive element having the NTC characteristics is series-connected to the detecting coil L3, the temperature compensating effect may be further enhanced.

[10] In place of the thermosensitive element for temperature compensation, it is also conceivable to construct the coils L1, L3 from wires whose resistance have a low temperature coefficient, such as manganin (Mn-Ni-Cu alloy) wires. This feature too may minimize the influence from the temperature under ordinary application conditions ranging approximately between—20° C. and 60° C.

Figure 10:
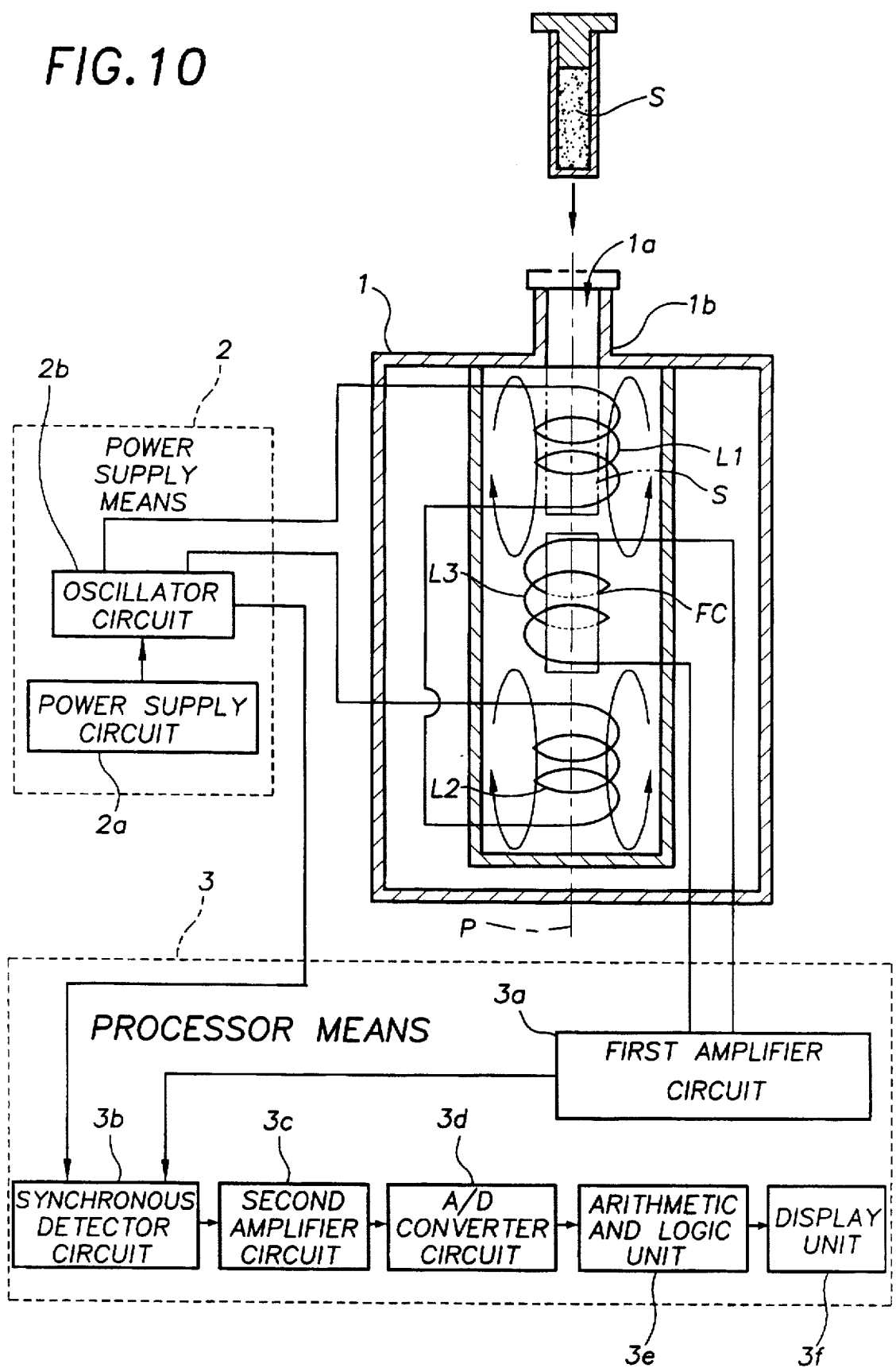
FIG. 10 is a schematic construction view of a magnetic powder concentration determining apparatus relating to a still further embodiment of the invention.

[11] Further, as the measuring means of the further embodiment [8], the construction of the first embodiment may be used, as shown in FIG. 10.

Figure 11:
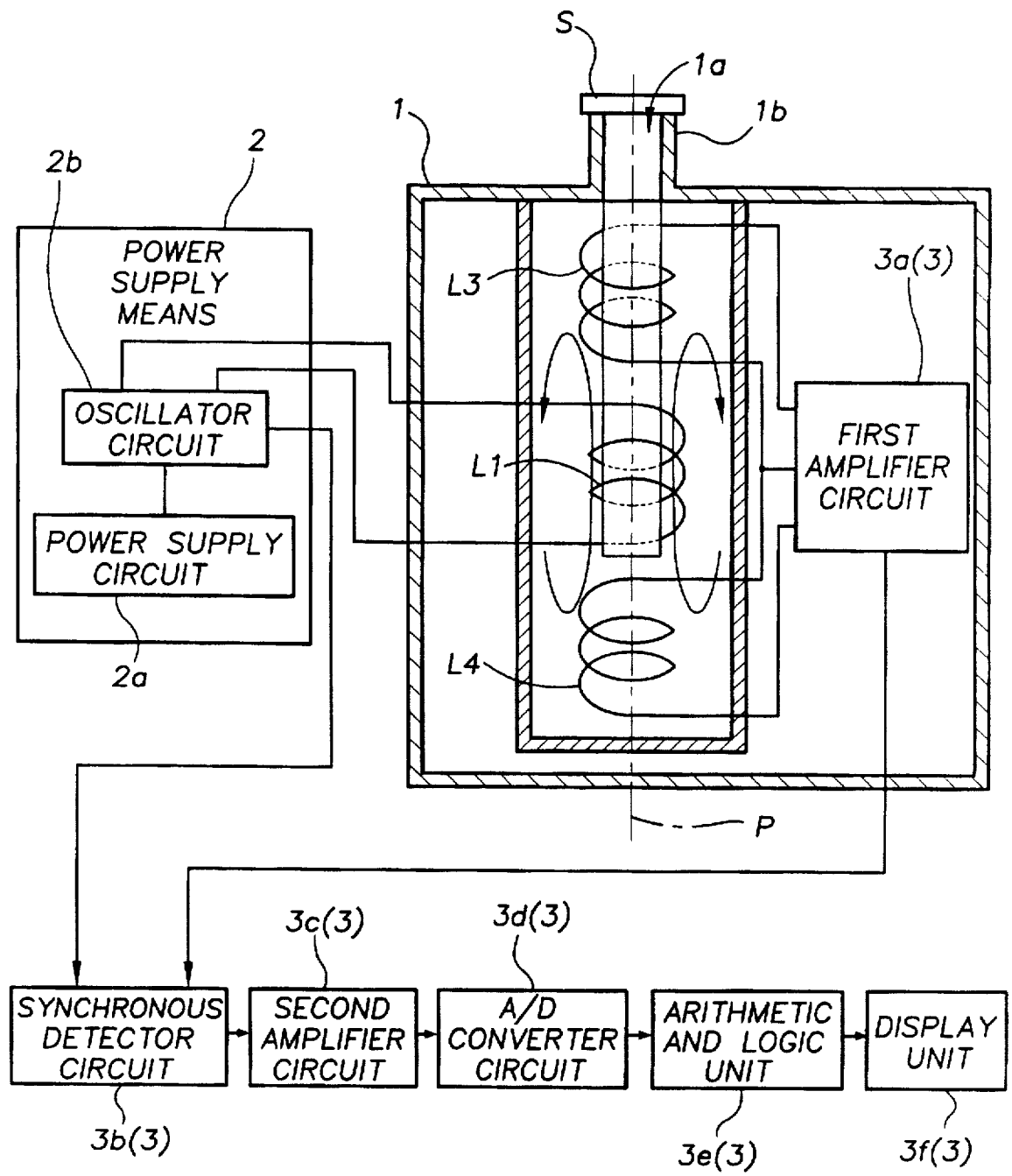
FIG. 11 is a schematic construction view of a magnetic powder concentration determining apparatus relating to a still further embodiment of the invention.
Figure 12:
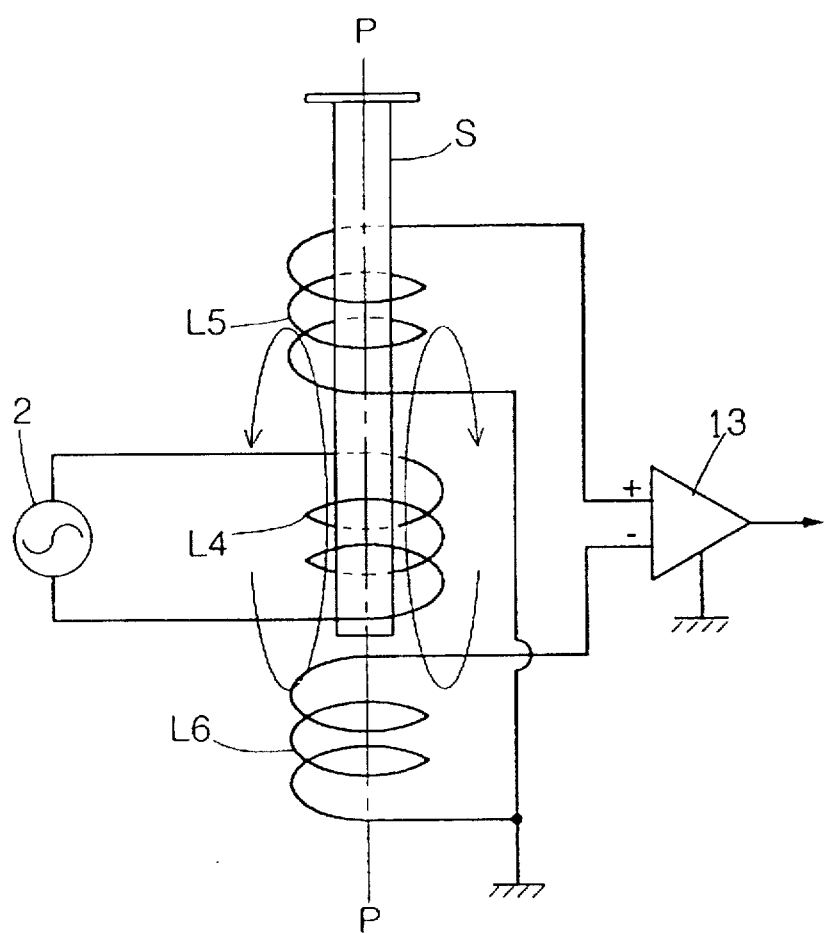
FIG. 12 is a diagram illustrating operation principle of a conventional apparatus.

[12] Also, as shown in FIG. 11, the temperature compensating constructions of the above alternative embodiments may be used in combination with the differential-detecting type electromagnetic induction construction including a single exciting coil L1 interposed between a pair of detecting coils L3, L4.

[13] The power source means for supplying the exciting power to the exciting coil in the above embodiments is not limited to such source means which outputs a sine-wave current. Instead, this power source means may comprise a more inexpensive square-wave current generating source including such components as a power supply circuit incorporating a dry cell, an oscillator circuit having an oscillator, a dividing circuit for dividing the output of the oscillator circuit, and a driver circuit connected to an output terminal of the divider circuit.

In this case, if the oscillator circuit is constructed by parallel-connecting a capacitor element to the detecting coil, it is possible to readily obtain a sine-wave output while avoiding noise generation due to parasitic oscillation which would result in the output from the detecting coil alone. And, if this output is detected in synchronism with the power output, an output of higher precision may be obtained.

The invention may be embodied in other specific forms without departing from the spirit or essential characteristics thereof. The present embodiments are therefore to be considered in all respects as illustrative and not restrictive, the scope of the invention being indicated by the appended claims rather than the foregoing description and all changes which come within the meaning and range of equivalency of the claims are therefore intended to be embraced therein.

What is claimed is:

1. A method of determining a concentration of magnetic powderly material in a sample, comprising
   arranging a pair of series-connected exciting coils relative to each other such that the respective exciting coils excite magnetic fields in directions opposed to each other;
   disposing a detecting coil at a position where the magnetic fields from the pair of exciting coils cancel out each other;
   inserting a sample mixed with magnetic powder into only one of the pair of exciting coils;
   detecting a voltage induced in the detecting coil in association with the insertion of the sample into the exciting coil; and
   determining the concentration of the magnetic powder in the sample based on the detected voltage.

2. A method according to claim 1, comprising the further steps of:
   disposing a core within the detecting coil with the core being position-adjustable along the axis of the detecting coil; and
   calibrating the zero point of the voltage induced in the detecting coil by adjusting the axial position of the core therein, and then effecting said step of inserting the sample into one of the exciting coils.

3. A method according to claim 1, comprising the further steps of:
   detecting insertion or non-insertion of the sample into the exciting coil;
   obtaining zero-point calibrating data when no sample insertion is detected; and effecting an automatic zero-point calibration when sample insertion is detected, based on the zero-point calibrating data obtained immediately prior to the detection of sample insertion.

4. A method according to claim 3, wherein the magnetic powder concentration in the sample is determined based on a voltage induced in the detecting coil upon completion of the insertion of the sample into the exciting coil or upon lapse of a predetermined time period after the insertion of the sample into the exciting coil.

5. An apparatus for determining a concentration of magnetic powder in a sample, comprising:

a pair of series-connected exciting coils arranged relative to each other such that the respective exciting coils excite magnetic fields in directions opposed to each other, wherein one of said exciting coils is capable of receiving therein the sample mixed with magnetic powder;

a detecting coil disposed at a position where the magnetic fields generated from the pair of exciting coils cancel each other; and measuring means for measuring a voltage induced in the detecting coil in association with insertion of the sample into the one exciting coil, the magnetic powder concentration being derived from the measured induced voltage.

6. An apparatus according to claim 5, further comprising a core which is disposed within the detecting coil to be position-adjustable along the axis of the detecting coil.

7. An apparatus according to claim 6, wherein said measuring means is an AC voltmeter.

8. An apparatus according to claim 5, further comprising:

processor means for outputting the magnetic powder concentration in the sample based on the voltage induced in the detecting coil;

sample detecting means for detecting insertion or non-insertion of the sample into the exciting coil; and calibrating means capable of inputting zero-point calibrating data when the sample detecting means detects non-insertion of the sample and then effecting automatic zero-point calibration when the sample detecting means detects insertion of the sample, based on the zero-point calibrating data inputted immediately prior to this detection of sample insertion by the sample detecting means.

9. An apparatus according to claim 8, wherein said processor means outputs the magnetic powder concentration based on a voltage induced in the detecting coil upon completion of the insertion of the sample into the exciting coil or upon lapse of a predetermined time period after the insertion of the sample into the exciting coil.

10. An apparatus according to claim 5, wherein the one exciting coil is series-connected with a thermosensitive element having NTC characteristics so as to maintain constant the current in the exciting coil against variation in the ambience temperature.

11. An apparatus according to claim 5, wherein a power source for supplying exciting power to the one exciting coil is comprised of a constant-current source.

12. An apparatus according to claim 5, wherein the exciting coil is formed of a wire whose resistance has a temperature coefficient of $5 \times 10^{-5}$ or less.

13. An apparatus according to claim 5, wherein a power source for the exciting coil outputs a square wave current, and the detecting coil constitutes a part of an oscillator circuit.

14. An apparatus for determining a concentration of magnetic powder in a sample, comprising:

a pair of series-connected exciting coils capable of exciting arranged such a manner that magnetic fields generated respectively therefrom oppose to each other, one of the exciting coils being capable of receiving therein the sample mixed with magnetic powder;

a detecting coil disposed at a position where the magnetic fields generated from the pair of exciting coils cancel each other;

measuring means for measuring a voltage induced in the detecting coil in association with insertion of the sample into the one exciting coil, the magnetic powder concentration being derived from the measured induced voltage; and a core that is disposed within the detecting coil to be position adjustable along the axis of the detecting coil.

15. An apparatus according to claim 14, wherein said measuring means is an AC voltometer.

16. An apparatus according to claim 14, wherein further comprising;

processor means for outputting the magnetic powder concentration in the sample based on the voltage induced in the detecting coil;

sample detecting means for detecting insertion or non-insertion of the sample into the exciting coil; and calibrating means capable of inputting zero-point calibrating data when the sample detecting means detects non-insertion of the sample and then effecting automatic zero-point calibration when the sample detecting means detects insertion of the sample, based on the zero-point calibrating data inputted immediately prior to this detection of sample insertion by the sample detecting means.

17. An apparatus according to claim 16, wherein said processor means outputs the magnetic powder concentration based on a voltage induced in the detecting coil upon completion of the insertion of the sample into the exciting coil.

18. An apparatus according to claim 16, wherein said processor means outputs the magnetic powder concentration based on a voltage induced in the detecting coil upon lapse of a predetermined time period after insertion of the sample into the exciting coil.

19. An apparatus according to claim 14, wherin one exciting coil is series-connected with a thermosensitive element.

20. An apparatus according to claim 14, wherein the exciting coil is formed of a wire whose resistance has a temperature coefficient of $5 \times 10^{-5}$ or less.

* * * * *

UNITED STATES PATENT AND TRADEMARK OFFICE
CERTIFICATE OF CORRECTION

PATENT NO. : 5,793,199
DATED : August 11, 1998
INVENTOR(S) : KASAHARA et al.

It is certified that error appears in the above-identified patent and that said Letters Patent is hereby corrected as shown below:

In column 1, line 21, between "air" and "acetylene" inset -- -- -- -- --.

In column 1, line 46, change "coiL" to -- coil --.

In column 4, line 53, change "2Δt" to -- αΔt --.

In column 4, line 54, change "2" to -- α --.

In column 5, line 23, change "parasitic" to -- parasistic --.

In column 12, line 23, change "parasitic" to -- parasistic --.

Signed and Sealed this

Seventh Day of September, 1999

Attest:

Q. TODD DICKINSON

Attesting Officer

Acting Commissioner of Patents and Trademarks